United States Patent
Kojoh et al.

(10) Patent No.: US 9,289,742 B2
(45) Date of Patent: Mar. 22, 2016

(54) EFFICIENT METHOD FOR DISPLAYING PROTEIN MULTIMER

(71) Applicant: GeneFrontier Corporation, Kashiwa-shi, Chiba (JP)

(72) Inventors: Kanehisa Kojoh, Kashiwa (JP); Takashi Kanamori, Kashiwa (JP); Shizue Katoh, Kashiwa (JP); Kumiko Tsuihiji, Kashiwa (JP)

(73) Assignee: GeneFrontier Corporation, Kashiwa (JP)

( * ) Notice: Subject to any disclaimer, the term of this patent is extended or adjusted under 35 U.S.C. 154(b) by 391 days.

(21) Appl. No.: 13/871,530

(22) Filed: Apr. 26, 2013

(65) Prior Publication Data

US 2013/0288930 A1 Oct. 31, 2013

Related U.S. Application Data

(60) Provisional application No. 61/638,774, filed on Apr. 26, 2012.

(51) Int. Cl.
| | |
|---|---|
| *C40B 50/06* | (2006.01) |
| *B01J 19/00* | (2006.01) |
| *C12N 9/00* | (2006.01) |
| *C07K 16/24* | (2006.01) |
| *C12N 15/10* | (2006.01) |

(52) U.S. Cl.
CPC ........... *B01J 19/0046* (2013.01); *C07K 16/241* (2013.01); *C12N 9/00* (2013.01); *C12N 15/1062* (2013.01); *C40B 50/06* (2013.01)

(58) Field of Classification Search
None
See application file for complete search history.

(56) References Cited

FOREIGN PATENT DOCUMENTS

| JP | 2001-500531 A | 1/2001 |
|---|---|---|
| WO | WO 98/56915 A2 | 12/1998 |
| WO | WO 2012/008211 A1 | 1/2012 |

OTHER PUBLICATIONS

Bird et al, *Science*, 242: 423-426 (Oct. 21, 1988).
Fujino et al., *Biochem. and Biophys. Research Comm.*, 428: 395-400 (2012).
Gebauer et al., *Curr. Opin. Chem. Biol.*, 13: 245-255 (2009).
Groves et al., *Expert Opinion on Biol. Therapy*, 5(1): 125-135 (2005).
Hanes et al., *Nature Biotech.*, 18(12): 1287-1292 (Dec. 2000).
He et al., *Expert Rev. of Proteomics*, 2(3): 421-430 (2005).

(Continued)

*Primary Examiner* — Christian Boesen
(74) *Attorney, Agent, or Firm* — Leydig, Voit & Mayer, Ltd.

(57) ABSTRACT

The invention provides a method of producing a protein multimer-nucleic acid complex comprising a protein multimer and any one target component of the protein multimer. A nucleic acid encoding the target component is subjected to in vitro translation to provide a translation product containing a target component-nucleic acid complex of the target component and the nucleic acid encoding the target component. A nucleic acid encoding a non-target component constituting the protein multimer together with the target component is translated into the non-target component by adding the nucleic acid encoding the non-target component to the previously provided translation product to provide the non-target component. The non-target component then is associated with the target component contained in the target component-nucleic acid complex to form a protein multimer, thus affording the protein multimer-nucleic acid complex of the protein multimer and the nucleic acid encoding the target component.

26 Claims, 1 Drawing Sheet

(56) References Cited

OTHER PUBLICATIONS

He et al., *Journal of Immunological Methods*, 231: 105-117 (1999).
Holliger et al., *Proc. Natl. Acad. Sci. USA*, 90: 6444-6448 (Jul. 1993).
Hudson et al., *Nature Medicine*, 9(1): 129-134 (Jan. 2003).
Huen et al., *Cell*, 131(5): 901-914 (Nov. 30, 2007).
Jendreyko et al., *J. Biol. Chem.*, 278(48): 47812-47819 (Nov. 28, 2003).
Kanamori et al., "Development of cell-free protein synthesis system suitable for ribosome display," poster presentation at 11th Annual Meeting of the Protein Science Society of Japan in Osaka, Japan (Jun. 7-9, 2011) summary English.
Kojoh et al., "In vitro affinity maturation based on Ribosome Display System with PUREfrex," poster presentation retrieved from Internet at www/genefrontier.com/wps/wp-content/uploads/2012/05/PEGS2012_posterl.pdf (Apr. 30, 2012).
Kojoh et al., "In vitro affinity maturation based on Ribosome Display System with PUREfrex," poster presentation at Protein and Antibody Engineering Summit in Boston, Massachusetts, USA (Apr. 30-May 4, 2012).
Kojoh et al., "In vitro selection from designed protein scaffold library with Ribosome Display on PURE system," GeneFrontier Corporation poster presentation, retrieved from Internet (May 9, 2001).
Kojoh et al., "In vitro selection from designed protein scaffold library with Ribosome Display on PURE system," poster presentation at Protein and Antibody Engineering Summit in Boston, Massachusetts, USA (May 9-13, 2011).
Kojoh et al., "In vitro selection from designed protein scaffold library with Ribosome Display on PURE system," poster presentation retrieved from Internet at www/genefrontier.com/PDF/Poster%20for%20PEGS.pdf (Sep. 2, 2011).
Kojoh et al., "In vitro selection from designed protein scaffold library with Ribosome Display on PURE system," poster presentation from 34th Annual Meeting of the Molecular Biology Society of Japan in Yokohama, Japan (Dec. 13-16, 2011).
Kojoh et al., "In vitro affinity maturation based on Ribosome Display System with PUREfrex," poster presentation from 35th Annual Meeting of the Molecular Biology Society of Japan in Fukuoka, Japan (Dec. 11-14, 2012).
Matsuura et al, *Orig. of Life and Evol. of the Biosph.*, 34: 151-157 (2004).
Melchionna et al., *J. Mol. Biol.*, 374: 641-654 (2007).
Marasco et al., *Pro. Natl. Acad. Sci. USA*, 90: 7889-7893 (1993).
Ohage et al., *J. Mol. Biol.*, 291: 1129-1134 (1999).
Ohashi et al., *Biochem and Biophys. Research Communications*, 352(1): 270-276 (2007).
Olson et al., *Protein Sci.*, 16: 476-484 (2007).
Parker et al., *Protein Eng., Des. & Sel.*, 18(9): 435-444 (2005).
Proba et al., *J. of Mol. Biol.*, 265: 161-172 (1997).
Shimizu et al., *Methods*, 36: 299-304 (2005).
Skerra, *Curr. Opin. Biotechnol.*, 18: 295-304 (2007).
Sumida et al., *Nucleic Acids Research*, 37(22): e147-1 (2009).
Ueda et al., *Methods in Molecular Bio.*, 607: 219-225 (2010).
Villemagne et al., *J. Immun. Methods*, 313: 140-148 (2006).
Visintin et al., *Proc. Natl. Acad. Sci. USA*, 96(21): 11723-11728 (Oct. 12, 1999).
Zahnd et al., *Nature Methods*, 4(3): 269-279 (Mar. 2007).
Zhou et al., *Mol. Cell*, 6: 751-756 (Sep. 2000).

SEQUENCE LISTING

```
<160> NUMBER OF SEQ ID NOS: 11

<210> SEQ ID NO 1
<211> LENGTH: 708
<212> TYPE: DNA
<213> ORGANISM: Artificial Sequence
<220> FEATURE:
<223> OTHER INFORMATION: cDNA encoding recombinant H chain

<400> SEQUENCE: 1
atggaggtgc aattggtgga gtctggggga ggcttggtac agcccggcag gtccctgaga      60
ctctcctgtg cggcctctgg attcaccttt gatgattatg ccatgcactg ggtccggcaa     120
gctccaggga agggcctgga atgggtctca gctatcactt ggaatagtgg tcacatagac     180
tatgcggact ctgtggaggg ccgattcacc atctccagag acaacgccaa gaactccctg     240
tatctgcaaa tgaacagtct gagagctgag gatacggccg tatattactg tgcgaaagtc     300
tcgtacctta gcaccgcgtc ctcccttgac tattgggggcc aagggaccct ggtcaccgtc     360
tcgagtgcta gcttcaaggg cccatcggtc ttccccctgg caccctcctc caagagcacc     420
tctgggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat ctgaattcga ctataaagat gacgatgaca ataatga                   708

<210> SEQ ID NO 2
<211> LENGTH: 675
<212> TYPE: DNA
<213> ORGANISM: Artificial Sequence
<220> FEATURE:
<223> OTHER INFORMATION: cDNA encoding recombinant L chain

<400> SEQUENCE: 2
atggatatcc agatgaccca gtctccatcc tccctgtctg catctgtagg ggacagagtc       60
accatcactt gtcgggcaag tcagggcatc agaaattact tagcctggta tcagcaaaaa     120
ccagggaaag cccctaagct cctgatctat gctgcatcca ctttgcaatc aggggtccca     180
tctcggttca gtggcagtgg atctgggaca gatttcactc tcaccatcag cagcctacag     240
cctgaagatt ttgcaactta ttactgtcaa aggtataacc gtgcaccgta tacttttggc     300
caggggacca aggtggaaat caaacgaact gtggcggcgc catctgtctt catcttcccg     360
```

```
ccatctgatg agcagttgaa atctggaact gcctctgttg tgtgcctgct gaataacttc      420
tatcctcgag aggccaaagt acagtggaag gtgataacg ccctccaatc gggtaactcc       480
caggagagtg tcacagagca ggacagcaag gacagcacct acagcctcag cagcaccctg      540
acgctgagca agcagatta cgagaaacac aaagtctacg cctgcgaagt cacccatcag       600
ggcctgagct cgcccgtcac aaagagcttc aacaggggag aggagcagaa gctgatctct      660
gaggaggatc tgcat                                                        675

<210> SEQ ID NO 3
<211> LENGTH: 116
<212> TYPE: DNA
<213> ORGANISM: Artificial Sequence
<220> FEATURE:
<223> OTHER INFORMATION: H chain 5' UTR

<400> SEQUENCE: 3
gaaattaata cgactcacta tagggagacc acaacggttt ccctctagaa ataattttgt       60
ttaactttaa gaaggagata taccaatgga ggtgcaattg gtggagtctg ggggag          116

<210> SEQ ID NO 4
<211> LENGTH: 121
<212> TYPE: DNA
<213> ORGANISM: Artificial Sequence
<220> FEATURE:
<223> OTHER INFORMATION: L chain 5' UTR

<400> SEQUENCE: 4
gaaattaata cgactcacta tagggagacc acaacggttt ccctctagaa ataattttgt       60
ttaactttaa gaaggagata taccaatgga tatccagatg acccagtctc catcctccct      120
g                                                                      121

<210> SEQ ID NO 5
<211> LENGTH: 57
<212> TYPE: DNA
<213> ORGANISM: Artificial Sequence
<220> FEATURE:
<223> OTHER INFORMATION: primer myc-g3p

<400> SEQUENCE: 5
gagcagaagc tgatctctga ggaggatctg catgaatatc aaggccaatc gtctgac          57

<210> SEQ ID NO 6
<211> LENGTH: 108
<212> TYPE: DNA
<213> ORGANISM: Artificial Sequence
<220> FEATURE:
<223> OTHER INFORMATION: primer g3p-SecMstop

<400> SEQUENCE: 6
ctcgagttat tcattaggtg aggcgttgag ggccagcacg gatgccttgc gcctggctta       60
tccagacggg cgtgctgaat tttgcgccgg aaacgtcacc aatgaaac                   108

<210> SEQ ID NO 7
<211> LENGTH: 48
<212> TYPE: DNA
<213> ORGANISM: Artificial Sequence
<220> FEATURE:
<223> OTHER INFORMATION: 5' primer

<400> SEQUENCE: 7
gaaattaata cgactcacta tagggagacc acaacggttt ccctctag                   48
```

```
<210> SEQ ID NO 8
<211> LENGTH: 31
<212> TYPE: DNA
<213> ORGANISM: Artificial Sequence
<220> FEATURE:
<223> OTHER INFORMATION: primer FLAG stop R

<400> SEQUENCE: 8
tcattatttg tcatcgtcat ctttatagtc g                              31

<210> SEQ ID NO 9
<211> LENGTH: 32
<212> TYPE: DNA
<213> ORGANISM: Artificial Sequence
<220> FEATURE:
<223> OTHER INFORMATION: primer SecMstop

<400> SEQUENCE: 9
ggattagtta ttcattaggt gaggcgttga gg                             32

<210> SEQ ID NO 10
<211> LENGTH: 25
<212> TYPE: DNA
<213> ORGANISM: Artificial Sequence
<220> FEATURE:
<223> OTHER INFORMATION: primer Realtime-F

<400> SEQUENCE: 10
gagcaaagca gattacgaga aacac                                     25

<210> SEQ ID NO 11
<211> LENGTH: 22
<212> TYPE: DNA
<213> ORGANISM: Artificial Sequence
<220> FEATURE:
<223> OTHER INFORMATION: primer Myc-R

<400> SEQUENCE: 11
cagatcctcc tcagagatca gc                                        22
```

EFFICIENT METHOD FOR DISPLAYING PROTEIN MULTIMER

CROSS-REFERENCE TO RELATED APPLICATIONS

This patent application claims the benefit of U.S. Provisional Patent Application No. 61/638,774 filed on Apr. 26, 2012, which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,290 bytes ASCII (Text) file named "713379SequenceListing.txt," created Apr. 24, 2013.

TECHNICAL FIELD OF THE INVENTION

The present invention relates to a method of efficiently preparing a complex containing a protein multimer and a nucleic acid in an in vitro translation system, which is used for selecting, from the gene library, a nucleic acid encoding a component contained in a protein multimer having a desired function.

BACKGROUND OF THE INVENTION

Monoclonal antibody which has been vastly developed as an antibody pharmaceutical product in recent years is a protein multimer consisting of H chain and L chain. Many improving techniques have been proposed in an attempt to enhance its drug efficacy and the like. For example, it has been shown that shuffling of the genes of H chain and L chain of an antibody is effective for improving the affinity of the antibody. That is, an antibody protein (e.g., Fab-type antibody) which is translated from the gene of either H chain library or L chain library and the corresponding partner chain are displayed in an in vivo selection system such as phage display (non-patent document 1: J. Mol. Biol., 1996.255.28-43, non-patent document 2: Biochem. Biophys. Res. Commun., 2002.295.31-36), yeast surface display (non-patent document 3: Protein Eng. Des. Sel., 2010.23.311-319) and the like, and selections are performed based on the affinity for the target antigen, whereby a clone with a higher affinity can be selected. In phage display and yeast surface display, however, a preparation of a library having diversity exceeding $10^{10}$ molecules is so hard that it requires substantial efforts and time, since the insertion efficiency of gene into an expression vector and the transformation efficiency of host cells are limited (generally $10^7$-$10^{10}$ molecules).

On the other hand, an in vitro selection system utilizing an in vitro translation system, which is represented by ribosome display (patent document 1: JP-A-2008-271903), is a technique for forming a complex of a gene (mRNA or cDNA) and a protein encoded by the gene in the in vitro translation system, and efficiently selecting a protein having a particular function. The essential element here is that the genotype and the phenotype correspond one-to-one. Specifically, cDNA or mRNA as a genotype needs to be physically bound one-to-one with a protein translated therefrom. Since a complex having a desired function is selected based on the properties of a protein phenotype, the number of the complexes shows the diversity of the library. Preparation of a complex in an in vitro selection system does not require a step of transformation of living cells, which is necessary for the in vivo selection system such as yeast surface display and the like, and can be achieved by the addition of a gene library to the in vitro translation system. Therefore, a library of complexes exceeding $10^{13}$ molecules can be easily prepared in the in vitro selection system, and a desired functional molecule can be selected using the library.

As mentioned above, the in vitro selection system is constituted by forming a one-to-one complex of a gene (mRNA or DNA) and a protein encoded by the gene by adding a gene library to an in vitro translation system. Therefore, if the protein to be selected is a protein multimer consisting of plural gene products, it is difficult to prepare a gene-protein complex.

SUMMARY OF THE INVENTION

When the affinity of an antibody, which is a representative protein multimer, is to be improved in an in vitro selection system, for example, L chain library is displayed on the ribosome and H chain is allowed to exist as a free protein in the same system to form an antibody, which is a heterodimer of L chain and H chain, and a complex containing antibody, ribosome and mRNA (i.e., ribosome display complex) needs to be formed finally in the system. In the ribosome display, ribosome, which is translating in vitro, needs to stably stay on the mRNA, and therefore, treatments such as removal of stop codon from L chain mRNA, addition of a sequence encoding translation elongation arrest sequence (arrest sequence) to the 3'-side of L chain mRNA, removal of a release factor or ribosome recycling factor from the in vitro translation system and the like are generally performed (patent document 1: JP-A-2008-271903). Meanwhile, since H chain needs to be translated as a free protein, treatments to keep ribosome on mRNA rather decrease the translation efficiency. Therefore, when mRNAs of H chain and L chain requiring different translation regulation are simultaneously translated in vitro within the same system, both the display efficiency of L chain on ribosome and the translation efficiency of H chain decrease, which in turn markedly decreases the formation efficiency of the ribosome display complex.

Accordingly, there is a demand for the development of a method of efficiently displaying a protein multimer such as antibody in an in vitro selection system capable of preparing libraries with high diversity, for example, ribosome display.

An object of the present invention is to provide a means for, in an in vitro selection system, more efficiently displaying a protein multimer, efficiently enhancing or improving functions (e.g., affinity and the like) of a protein multimer such as antibody and the like, or selecting a nucleic acid encoding a component contained in a protein multimer having a desired function.

The present inventors have conducted intensive studies in an attempt to solve the above-mentioned problems and found that the mRNA recovery rate after selection is drastically improved, by first forming a ribosome display complex containing a library gene (L chain of antibody here), and then expressing the pair protein gene (H chain of antibody here) in the same tube, or by performing formation of a ribosome display complex containing a library gene (L chain of antibody here) and synthesis of the pair protein gene (H chain of antibody here) in separate tubes, and mixing the reaction products in those tubes, compared to the case where L chain and H chain are simultaneously translated in the same tube.

More specifically, as a first step of the first embodiment, a spacer gene for ribosome display (geneIII, tolA and the like)

was ligated to the 3' side of the gene of L chain. Furthermore, a stop codon was removed from the spacer sequence, or the arrest sequence of *Escherichia coli* was added to the 3'-terminus of the spacer gene, and the obtained mRNA was added to an in vitro translation system, whereby a L chain-ribosome-mRNA of L chain ternary complex (ribosome display complex) was formed. As a second step, mRNA of H chain and ribosome prepared in advance were added to the reaction mixture containing the ribosome display complex to synthesize a free H chain, which was then associated with the L chain displayed on the ribosome display complex, whereby a ribosome display complex displaying the antibody consisting of H chain and L chain was finally formed with high efficiency.

In a second embodiment, the same reaction as in the first step of the above-mentioned first embodiment was performed in one tube, then H chain was synthesized by subjecting mRNA of H chain (or coding for H chain) to an in vitro translation system in a separate tube. When the reaction products in the two tubes were mixed, H chain was associated with the L chain displayed on the ribosome display complex, whereby a ribosome display complex displaying the antibody consisting of H chain and L chain was finally formed with high efficiency.

They have further studied based on these findings and completed the present invention. Accordingly, the present invention relates to the following.

[1] A method of producing a protein multimer-nucleic acid complex comprising the protein multimer and a nucleic acid encoding any one target component of the protein multimer, which comprises the following steps:
i) translating a nucleic acid encoding the target component into the target component by an in vitro translation system to give a translation product containing a target component-nucleic acid complex containing the target component and the nucleic acid encoding the target component, and
ii) translating a nucleic acid encoding a non-target component constituting the protein multimer together with the target component into the non-target component by adding the nucleic acid encoding the non-target component to the translation product obtained in i) to give the non-target component, associating the non-target component with the target component in the target component-nucleic acid complex to form the protein multimer, thus affording the protein multimer-nucleic acid complex comprising the protein multimer and the nucleic acid encoding the target component.

[2] The method of [1], wherein the in vitro translation system in i) does not comprise a nucleic acid encoding the non-target component.

[3] The method of [1] or [2], wherein the protein multimer-nucleic acid complex and the target component-nucleic acid complex comprise a ribosome.

[4] The method of any of [1]-[3], wherein ii) comprises adding a ribosome to the translation product obtained in i).

[5] The method of any of [1]-[4], wherein one molecule of the protein multimer and one molecule of the nucleic acid encoding the target component are contained per one molecule of the protein multimer-nucleic acid complex.

[6] The method of any of [1]-[5], wherein the in vitro translation system consists of independently purified factors.

[7] The method of [6], wherein at least one of the independently purified factors is a factor extracted from prokaryote.

[8] The method of any of [1]-[7], wherein the protein multimer is a dimer.

[9] The method of any of [1]-[8], wherein the protein multimer has a function as a multimer.

[10] The method of any of [1]-[9], wherein the protein multimer is an antibody.

[11] The method of [10], wherein the antibody is a Fab fragment.

[12] The method of [10] or [11], wherein the target component is one selected from the group consisting of an L chain and an H chain, and the non-target component is the other.

[13] The method of any of [1]-[12], wherein the nucleic acid encoding the target component is a library of the nucleic acid encoding the target component.

[14] A method of producing a library of a protein multimer-nucleic acid complex comprising the protein multimer and a nucleic acid encoding any one target component of the protein multimer, which comprises the following steps:
i) translating a library of nucleic acid encoding the target component into the target component by an in vitro translation system to give a translation product containing a library of a target component-nucleic acid complex containing the target component and the nucleic acid encoding the target component, and
ii) translating a nucleic acid encoding a non-target component constituting the protein multimer together with the target component into the non-target component by adding the nucleic acid encoding the non-target component to the translation product obtained in i) to give the non-target component, associating the non-target component with the target component in the target component-nucleic acid complex to form the protein multimer, thus affording the library of the protein multimer-nucleic acid complex comprising the protein multimer and the nucleic acid encoding the target component.

[15] A method of producing a protein multimer-nucleic acid complex comprising the protein multimer and a nucleic acid encoding any one target component of the protein multimer, which comprises the following steps:
i') translating the nucleic acid encoding the target component into the target component by an in vitro translation system to give a translation product containing a target component-nucleic acid complex containing the target component and the nucleic acid encoding the target component,
ii') translating a nucleic acid encoding a non-target component constituting the protein multimer together with the target component by an in vitro translation system to give a translation product containing the non-target component, and
iii') mixing the translation product of i') with the translation product of ii'), associating the non-target component with the target component contained in the target component-nucleic acid complex to form the protein multimer, thus affording the protein multimer-nucleic acid complex comprising the protein multimer and the nucleic acid encoding the target component.

[16] The method of [15], wherein the in vitro translation system in i') does not contain the nucleic acid encoding the non-target component.

[17] The method of [15] or [16], wherein the in vitro translation system in ii') does not contain the nucleic acid encoding the target component.

[18] The method of any of [15]-[17], wherein the protein multimer-nucleic acid complex and the target component-nucleic acid complex further comprise a ribosome.

[19] The method of any of [15]-[18], wherein one molecule of the protein multimer, and one molecule of the nucleic acid encoding the target component are contained per one molecule of the protein multimer-nucleic acid complex.

[20] The method of any of [15]-[19], wherein the in vitro translation system consists of independently purified factors.

[21] The method of [20], wherein at least one of the independently purified factors is a factor extracted from prokaryote.

[22] The method of any of [15]-[21], wherein the protein multimer is a dimer.
[23] The method of any of [15]-[22], wherein the protein multimer has a function as a multimer.
[24] The method of any of [15]-[23], wherein the protein multimer is an antibody.
[25] The method of [24], wherein the antibody is a Fab fragment.
[26] The method of [24] or [25], wherein the target component is one selected from the group consisting of an L chain and an H chain, and the non-target component is the other.
[27] The method of any of [15]-[26], wherein the nucleic acid encoding the target component is a library of the nucleic acid encoding the target component.
[28] A method of producing a library of a protein multimer-nucleic acid complex comprising the protein multimer and a nucleic acid encoding any one target component of the protein multimer, which comprises the following steps:
i') translating a library of a nucleic acid encoding the target component into the target component by an in vitro translation system to give a translation product containing a library of a target component-nucleic acid complex containing the target component and the nucleic acid encoding the target component,
ii') translating a nucleic acid encoding a non-target component constituting the protein multimer together with the target component by an in vitro translation system to give a translation product containing the non-target component, and
iii') mixing the translation product of i') with the translation product of ii'), associating the non-target component with the target component contained in the target component-nucleic acid complex to form the protein multimer, thus affording the library of the protein multimer-nucleic acid complex comprising the protein multimer and the nucleic acid encoding the target component.

Effect of the Invention

According to the present invention, a nucleic acid encoding a component contained in a protein multimer having a desired function can be selected with a high efficiency from the library, since the protein multimer can be efficiently displayed on a display complex. By performing in vitro selection such as a ribosome display, an mRNA display and the like using the present invention, the function such as binding affinity and the like of a complicated protein multimer such as antibody and the like can be increased or improved efficiently.

DESCRIPTION OF EMBODIMENTS

In the first embodiment, the present invention provides a method of producing a protein multimer-nucleic acid complex comprising the protein multimer and a nucleic acid encoding any one target component of the protein multimer, which comprises the following steps:
i) translating the nucleic acid encoding the target component into the target component by an in vitro translation system to give a translation product containing a target component-nucleic acid complex containing the target component and the nucleic acid encoding the target component, and
ii) translating a nucleic acid encoding a non-target component constituting the protein multimer together with the target component into the non-target component by adding the nucleic acid encoding the non-target component to the translation product obtained in i) to give the non-target component, associating the non-target component with the target component in the target component-nucleic acid complex to form the protein multimer, thus affording the protein multimer-nucleic acid complex comprising the protein multimer and the nucleic acid encoding the target component.

In the second embodiment, the present invention provides a method of producing a protein multimer-nucleic acid complex comprising the protein multimer and a nucleic acid encoding any one target component of the protein multimer, which comprises the following steps:
i') translating the nucleic acid encoding the target component into the target component by an in vitro translation system to give a translation product containing a target component-nucleic acid complex containing the target component and the nucleic acid encoding the target component,
ii') translating a nucleic acid encoding a non-target component constituting the protein multimer together with the target component by an in vitro translation system to give a translation product containing the non-target component, and
iii') mixing the translation product of i') with the translation product of ii'), associating the non-target component with the target component contained in the target component-nucleic acid complex to form the protein multimer, thus affording the protein multimer-nucleic acid complex comprising the protein multimer and the nucleic acid encoding the target component.

The method of the present invention enables, in a display technique utilizing an in vitro translation system, selection of a nucleic acid encoding a component contained in the multimer by physically linking one-to-one the protein multimer and the nucleic acid encoding the component contained in the protein multimer, based on the activity of the whole protein multimer (affinity for particular substance etc.) rather than the activity of a single component.

Examples of the display technique utilizing an in vitro translation system include ribosome display (Proc. Natl. Acad. Sci. USA, 91, 9022-9026, 1994; Proc. Natl. Acad. Sci. USA, 94, 4937-4942, 1997; JP-A-2008-271903), mRNA display (FEBS Lett., 414.405-408, 1997), CIS display (Proc. Natl. Acad. Sci. USA, 101, 2806-2810, 2004), Covalent antibody display (Nucleic Acids Res., 33(1), e10, 2005) and the like. The method of the present invention can be utilized in any display technique as long as it contains a step of translating a nucleic acid encoding a protein of interest into the protein to prepare a complex containing the protein and the nucleic acid encoding the protein, and corresponding, one-to-one, the protein and the nucleic acid encoding the protein.

Examples of other method utilizing an in vitro translation system include a STABLE method (FEBS Lett., 457, 227-230, 1999), a microbeads display method (FEBS Lett., 532, 455-458, 2002) and the like. They can commonly correspond to a gene of a target component and the target component by transcribing and translating the gene in a reversed-phase emulsion. Unlike the aforementioned non-encapsulated type methods (ribosome display, mRNA display, CIS display and Covalent antibody method), these methods can transcribe and translate a gene and correspond the completed target component to the gene in an encapsulated space of a reversed-phase emulsion, without a special gene alteration such as addition of the arrest sequence, deletion of a stop codon and the like.

When a target component constitutes a protein multimer, therefore, application of the present invention is not entirely necessary. Accordingly, the method of the present invention is preferably used when the in vitro translation system is of a non-encapsulated type.

In the present specification, the "protein multimer" means a multimer wherein the same or different, two or more proteins are linked directly or via a linker. The linkage between the proteins may be made by a covalent bond or a non-covalent interaction. Examples of the linker include a disulfide bond formed by a reaction between cysteine residues in proteins and the like. In contrast, when a linker is not present, the multimer may be simply formed by the affinity between proteins (hydrogen bond interaction, hydrophobic bond interaction etc.).

In the present invention, the protein multimer is a hetero or homo multimer, preferably a hetero multimer. While the number of components contained in a protein multimer is not particularly limited, the protein multimer can be a dimer, a trimer, a tetramer, a hexamer and the like, preferably a dimer.

Examples of the protein multimer include extracellularly secreted proteins and proteins on a cellular membrane such as antibody, ligand, adhesion molecule, pump, channel, receptor and the like, intracellular proteins such as signaling factor, nuclear receptor, transcription factor and the like. They are not particularly limited as long as they can form a multimer in an in vitro translation system, and have a particular function as a multimer (for example, affinity for particular substance). The protein multimer is preferably an antibody.

In the present specification, the "antibody" is used as one encompassing a full-length antibody and an antigen binding fragment (i.e., "antigen binding portion") thereof, which is a protein multimer. The "antibody" refers to a protein multimer containing at least one H chain and one L chain or an antigen binding portion thereof, which is a protein multimer.

In the present specification, the "antigen binding portion" of an antibody is used as one referring to one or more fragments of an antibody retaining an ability to specifically bind to an antigen. It has been clarified that the antigen binding function of an antibody is performed by a fragment of a full-length antibody. Examples of the "antigen binding portion" of an antibody include (i) Fab fragment, a monovalent fragment constituted by $V_L$, $V_H$, $C_L$ and $C_{H1}$ domains, (ii) $F(ab')_2$ fragment, a divalent fragment containing two Fab fragments linked by disulfide bond in the hinge region, (iii) Fab' fragment, an inherent Fab having a hinge region portion (see FUNDAMENTAL IMMUNOLOGY, Paul ed., 3.sup.rd ed. 1993) and the like. The antigen binding portion generally contains at least one H chain and at least one L chain. The Fab fragment is a protein dimer constituted by one H chain and one L chain. The $F(ab')_2$ fragment is a protein tetramer constituted by two H chains and two L chains. The Fab' fragment is a protein dimer constituted by one H chain and one L chain.

In the present invention, the antibody is preferably a Fab fragment.

The method of the present invention includes a step of obtaining a translation product containing a target component-nucleic acid complex containing the target component and the nucleic acid encoding the target component, by translating a nucleic acid encoding any one component of interest (target component) among components constituting a protein multimer into the target component by an in vitro translation system (step i) or step i')). For example, when an antibody-nucleic acid complex containing the antibody, and the nucleic acid encoding any one chain (target chain) (for example, L chain) selected from the group consisting of H chain and L chain constituting the antibody is to be produced by the method of the present invention, a nucleic acid encoding the target chain is translated into the target chain to give a translation product containing the target chain-nucleic acid complex containing the target chain, and the nucleic acid encoding the target chain.

In the present specification, the "in vitro translation system" refers to a protein synthesis system using a reaction mixture comprising factors necessary for protein synthesis such as cell extract and the like, without the need for living cells, and is also referred to as a cell-free protein synthesis system. That is, the in vitro translation system is characterized in that the living cells are not required in translating an mRNA into a protein. The in vitro translation system in the present invention includes a system for performing translation and a system for performing transcription and translation. Hence, the in vitro translation system of the present invention encompasses any of the following embodiments:
(1) translating an mRNA into a protein; and
(2) transcribing a DNA into an mRNA, and further translating the mRNA into a protein.

The in vitro translation system includes an in vitro translation system using a cell extract of *Escherichia coli*, wheat germ, rabbit reticulocyte, cultured cell and the like, and a reconstituted in vitro translation system constituted from independently purified factors. The in vitro translation system to be used in the present invention is preferably a reconstituted in vitro translation system constituted from independently purified factors. Preferable examples of the reconstituted in vitro translation system include a PURE system (JP-B-4061043, JP-A-2009-112286, Y. Shimizu et al., (2001) Nat. Biotechnol., vol. 19, p. 751-755, JP-A-2008-271903, E. Osada et al., (2009) J. Biochem., vol. 145, p. 693-700). This reconstituted in vitro translation system can prevent contamination of nuclease and protease more easily than the in vitro translation system using a cell extract, and therefore, can improve the efficiency of the translation from a nucleic acid encoding a target component into the target component. In addition, a target component-nucleic acid complex containing the target component and the nucleic acid encoding the target component can be stably formed and maintained. Finally, therefore, the desired protein multimer-nucleic acid complex can be obtained efficiently.

In the present specification, the "factors" refers to a building block of an in vitro translation system that can be purified independently. The factors include single proteins and substrates. Furthermore, various complexes and mixtures that can be isolated from a crude fraction are also included. For example, factors to be purified as a complex include multimer of proteins, ribosomes and the like. Mixtures include tRNA mixture and the like. The "independently purified factors" refer to factors that have been each independently purified from other factors. It is possible to reconstitute and construct an in vitro translation system by mixing as required the independently purified factors necessary for protein synthesis. Factors that present in a mixed fraction containing a plurality of kinds of factors without being isolated from the cell extract are not said to be independently purified factors. Even in the case of a complex consisting of a plurality of components, the complex is "independently purified factors" in the present specification, provided that it has been purified as single factors. For example, a purified ribosome is a complex consisting of several elements, and it is an "independently purified factor" because it can be purified as a single factor.

Independently purified factors can be obtained by purifying from extracts of a wide variety of cells. Cells for purifying the factors include, for example, prokaryotic cells and eukaryotic cells. Prokaryotic cells include *Escherichia coli* cells, extreme-thermophilic bacterial cells, and *Bacillus subtilis* cells. Eukaryotic cells include yeast cells, plant cells, insect cells, and mammalian cells. In particular, when the independently purified factors consist of a protein only, each factor can be obtained by one of the methods shown below.
(1) Isolating a gene that encodes each factor (protein) and introducing into an expression vector, after which an appropriate host cell is transformed therewith to express the factor, and the expressed factor is recovered.
(2) Isolating a gene that encodes each factor, synthesizing the factor using an in vitro translation system, and recovering it.
In (1), first, an expression plasmid is prepared by inserting the gene for each factor into an expression vector comprising an expression regulatory region so that the desired factor will be expressed under the control of the region. An expression regulatory region that constitutes the vector refers to, for example, an enhancer, a promoter, a terminator and the like. The expression vector can comprise a drug resistance marker and the like. Next, host cells are transformed with this expression plasmid to allow each factor to be expressed.

The in vitro translation system preferably used for the method of the present invention consists of purified factors. In the present invention, the in vitro translation system can contain, for example, the following factors in an independently purified state:
an initiation factor (IF),
an elongation factor (EF),
a release factor (RF),
an aminoacyl-tRNA synthetase (AARS),
a ribosome,
an amino acid,
a nucleoside triphosphate, and
a tRNA.

These factors are not limited to those derived from prokaryotic cells such as *Escherichia coli*, and those derived from eukaryotic cells can also be used.

By adding the factors that constitute the above-described in vitro translation system to a buffer solution that maintains a pH suitable for the transcription and translation, a composition having an in vitro translation activity can be obtained. Suitable pH is, for example, pH 6 to pH 9, preferably pH 7 to 8. Buffer solutions which can be used in the present invention include potassium phosphate buffer solution (pH 7.3), Hepes-KOH (pH 7.6) and the like.

A salt can also be added to the composition having an in vitro translation activity for the purpose of protecting factors and maintaining the activity thereof. Specifically, potassium glutamate, potassium acetate, ammonium chloride, magnesium acetate, magnesium chloride, calcium chloride and the like can be mentioned.

Other low-molecular weight compounds can be added to the composition having an in vitro translation activity as an enzyme substrate and/or for the purpose of improving and maintaining the activity of each factor. Specifically, polyamines such as putrescine and spermidine, reducing agents such as dithiothreitol (DTT) and the like can be added to the composition.

In the case of an in vitro translation system using factors derived from prokaryotic cells such as of *Escherichia coli*, it is preferable that a composition having an in vitro translation activity further comprises ribosome recycling factor (RRF), methionyl-tRNA transformylase (MTF) and 10-formyl 5,6,7,8-tetrahydrofolate (FD).

When a DNA is transcribed into an mRNA and the mRNA is translated into a polypeptide, a composition having an in vitro translation activity can contain an RNA polymerase for transcription to the mRNA. Specifically, the RNA polymerases shown below can be utilized in the present invention. These RNA polymerases are commercially available.
T7 RNA polymerase
T3 RNA polymerase
SP6 RNA polymerase The composition having an in vitro translation activity can comprise, in addition to factors for transcription and translation, an additional factor. Additional factors include, for example, the factors shown below.
Enzymes for recycling energy in the reaction system: creatine kinase,
myokinase, and
nucleoside diphosphate kinase and the like;
substrates for enzymes for recycling energy in the reaction system:
creatine phosphate and the like;
enzymes for degradating inorganic pyrophosphoric acid resulting from transcription/translation:
inorganic pyrophosphatase and the like.

In the composition having an in vitro translation activity, it is preferable that at least one of the independently purified factors be extracted from a prokaryote. In one embodiment, at least one, preferably all, selected from the group consisting of an initiation factor, an elongation factor, a release factor, an aminoacyl-tRNA synthetase, a ribosome and a tRNA, contained in the composition having an in vitro translation activity have been extracted from a prokaryote (for example, a Gram-negative bacterium, preferably *Escherichia coli*). In one embodiment, the composition having an in vitro translation activity consists of independently purified factors, and all of the factors are extracted from a prokaryote (for example, a Gram-negative bacterium, preferably *Escherichia coli*).

The constitution of the composition having an in vitro translation activity can be adjusted as appropriate according to the kind of the protein to be synthesized, as well as to the above-described basic constitution. For example, in the case of a protein unlikely to form a higher-order structure, an in vitro translation system supplemented with a class of proteins called molecular chaperones can be used. Specifically, an in vitro translation system supplemented with Hsp100, Hsp90, Hsp70, Hsp60, Hsp40, Hsp10, small Hsp, a homologue thereof, *Escherichia coli* trigger factor and the like can be mentioned. Molecular chaperones are proteins known to assist protein folding to form a higher-order structure in cells to prevent the protein from aggregating (Bukau and Horwich, Cell (1998) vol. 92, p. 351-366, Young et al., Nat. Rev. Mol. Cell Biol (2004) vol. 5, p. 781).

When a disulfide bond is formed between components of a protein multimer or in the molecules of a component, like antibody, the redox potential of the reaction mixture is important. For this reason, the reducing agent DTT may be removed from the reaction mixture, or a composition supplemented with a reagent that controls the redox potential such as oxidized glutathione may be used. Furthermore, it is possible to use a composition supplemented with an enzyme that promotes the formation of disulfide bond, or isomerizes the disulfide bond correctly. Specifically, such enzymes include protein disulfide isomerase (PDI), which is present in the endoplasmic reticulum of eukaryotic cells, DsbA from *Escherichia coli*, DsbC and the like.

The purification methods of each factor contained in the reconstituted composition having an in vitro translation activity and more detailed constitution of the composition having an in vitro translation activity are described in JP-A-2008-271903, JP-A-2003-10249 and the like, and are known to those of ordinary skill in the art. In addition, compositions having the in vitro translation activity are commercially available from plural companies and can be obtained easily.

A translation product containing a target component-nucleic acid complex containing the target component and the nucleic acid encoding the target component can be obtained by adding the nucleic acid encoding the target component to the above-mentioned composition having an in vitro translation activity, and incubating the mixture at a temperature at which the in vitro translation proceeds, thus translating the nucleic acid into the target component. While the incubation time is not particularly limited as long as it is sufficient for completion of the translation of the nucleic acid into the target component, it is generally about 5-240 min.

What is important here is that the in vitro translation in steps i) and i') is performed in the absence of a nucleic acid encoding a non-target component constituting the protein multimer together with the target component. Thus, a protein multimer-nucleic acid complex can be produced highly efficiently by first performing the translation into a target component, and thereafter, in the presence of the translation product, performing the translation into a non-target component, or by performing the translation into the target component and that into the non-target component in separate reaction systems, and thereafter mixing all translation products.

In the present specification, the "nucleic acid" refers mainly to a polymer of a deoxyribonucleotide or ribonucleotide. Hence, the nucleic acid is a deoxyribonucleic acid (DNA) or a ribonucleic acid (RNA). Furthermore, the nucleic acids in the present invention can comprise nucleotide derivatives having a non-natural base. The nucleic acids can also comprise peptide nucleic acids (PNAs). As far as a translation into an encoded target component can be performed by an in vitro translation system, the building block of the nucleic acid may be any one of these nucleic acids or a mixture thereof. Therefore, DNA-RNA hybrid nucleotides are included in the nucleic acids in the present invention. Alternatively, a chimeric nucleic acid generated by connecting different nucleic acids, like DNA and RNA, into a single strand is also included in the nucleic acids in the present invention. The structure of any nucleic acid in the present invention is not limited, as far as a translation into an encoded target component can be performed by an in vitro translation system. Specifically, the nucleic acid can assume a structure such as a single strand, double strand, or triple strand. The nucleic acid to be used in the method of the present invention is preferably an mRNA or cDNA encoding the target component.

When a prokaryote (such as *Escherichia coli* and the like)-derived ribosome is utilized in an in vitro translation system, a nucleic acid encoding the target component preferably contains the Shine-Dalgarno (SD) sequence, which is a ribosome-binding sequence, at the upstream of the initiation codon. When the SD sequence is contained, the efficiency of the translation increases.

To form a stable target component-nucleic acid complex containing the target component, and the nucleic acid encoding the target component, it is preferable to modify the nucleic acid encoding the target component. As a technique to form a stable protein-nucleic acid complex, ribosome display (Proc. Natl. Acad. Sci. USA, 91, 9022-9026, 1994; Proc. Natl. Acad. Sci. USA, 94, 4937-4942, 1997; JP-A-2008-271903), mRNA display (FEBS Lett., 414.405-408, 1997), CIS display (Proc. Natl. Acad. Sci. USA, 101, 2806-2810, 2004), Covalent antibody display (Nucleic Acids Res., 33(1), e10, 2005) and the like can be mentioned. The constitution of the target component-nucleic acid complex formed changes according to the modification of the nucleic acid encoding the target component.

In ribosome display (Proc. Natl. Acad. Sci. USA, 91, 9022-9026, 1994; Proc. Natl. Acad. Sci. USA, 94, 4937-4942, 1997; JP-A-2008-271903), the nucleic acid (preferably mRNA) encoding the target component preferably has at least one (preferably two, more preferably all) of the following characteristics to improve the selection efficiency.
(1) Containing a sequence encoding a spacer at the downstream of the target gene.
(2) Containing the arrest sequence such as partial sequence of SecM and the like at the downstream of the spacer.
(3) Removing a stop codon.

In ribosome display, a sequence that encodes a spacer is preferably contained at the downstream of the gene of the target component. The spacer prevents steric hindrance between the newly generated polypeptide and the ribosome by providing a sufficient space for the translated polypeptide to be accurately folded outside of the ribosome. Here, without a spacer of sufficient length, the desired polypeptide (target component) is unable to go out completely from the ribosome, so that selection by ribosome display cannot be performed efficiently. The spacer consists of at least 20 amino acids, preferably 30 amino acids or more, more preferably 40 amino acids or more in length. Specifically, a partial sequence of the phage gene III, a partial sequence of *Escherichia coli* tolA and the like can be used.

Furthermore, a nucleic acid (preferably, mRNA) having a sequence that encodes *Escherichia coli* SecM translation elongation arrest sequence (arrest sequence; amino acid residues 148 to 170) placed downstream of the spacer sequence is preferably used. This translation elongation arrest sequence has been shown to firmly interact with the peptide tunnel in ribosome (Nakatogawa et al., Cell (2002) vol. 108, p. 629-636), and has been proven to efficiently stop the elongation of the translation when using a reconstituted in vitro translation system (Muto et al., Mol. Cell (2006) vol. 22, p. 545-552). A stable target component-ribosome-mRNA ternary complex can be formed by tight interaction of ribosome and translation elongation arrest sequence of SecM.

A nucleic acid (preferably, mRNA) with such a structure can be obtained by, for example, inserting the gene of the target component into an expression vector harboring a 5' UTR sequence comprising a promoter sequence and the SD sequence, or a 3' terminal spacer sequence, and transcribing the same using RNA polymerase. Generally, RNA polymerase recognizes a region comprising a particular sequence called a promoter, and synthesizes an mRNA on the basis of the nucleic acid sequence of the DNA placed downstream thereof. It is also possible to construct a transcription template having the desired structure by utilizing PCR without using an expression vector (Split-Primer PCR method, Sawasaki et al., PNAS (2002) vol. 99, p. 14652-14657). In this method, a template DNA is constructed by adding a 5' UTR sequence and a spacer sequence to the desired DNA by PCR. In preparing an mRNAs library from a DNA library, it is unnecessary to clone a DNA into the above-described vector. For this reason, time and labor can be saved.

How to construct a template DNA by PCR is specifically exemplified below.
(1) The DNA region that encodes the target component is amplified from an appropriate library and the like by a PCR using a primer comprising a 5' UTR sequence comprising a promoter and the SD sequences and a primer comprising a portion of a spacer sequence and removing a stop codon.
(2) The amplified DNA is again amplified with the primer for the 5' UTR portion and a primer comprising a spacer portion and SecM sequence.

By further amplifying the DNA thus constructed as required, and performing transcription using RNA polymerase with the amplified DNA as the template, an mRNA that serves as the template for the translation can be obtained.

The mRNA transcribed by RNA polymerase is recovered as required, and added to a composition having an in vitro translation activity. The transcribed mRNA can be recovered by ethanol precipitation after phenol treatment. Commercially available RNA extraction kits such as RNeasy (manufactured by Qiagen) can be utilized for recovering the mRNA.

Also, the above-described DNA itself comprising the nucleic acid sequences necessary for the transcription and translation incorporated in the gene of the target component can also be used as the template. In this case, the DNA is transcribed into an mRNA using the composition having an in vitro translation activity comprising RNA polymerase, and the mRNA is translated into a polypeptide to form the ternary complex.

In mRNA display (FEBS Lett., 414.405-408, 1997), puromycin is added to the 3'-terminal of the nucleic acid (preferably mRNA) encoding the target component. Puromycin can be added to a nucleic acid (preferably mRNA) by a method utilizing UV crosslinkage (Nucleic Acids Res., 28, e83, 2000) or a method utilizing hybridization of primer (FEBS Lett., 508, 309-312, 2001). By subjecting a nucleic acid (preferably mRNA) encoding a target component, wherein puromycin is added to the 3' terminus, to an in vitro translation, a complex, wherein the translated target component and the nucleic acid (preferably, mRNA) are covalently bound via puromycin, can be formed.

In the nucleic acid (preferably mRNA) encoding the target component to be used for CIS display (Proc. Natl. Acad. Sci. USA, 101, 2806-2810, 2004), RepA gene is fused in-frame to the 3' terminal of the coding region of the target component, and the CIS element is further fused to the downstream thereof. By in vitro translation using this nucleic acid as a template, a fusion protein of the target component and RepA is produced, and RepA contained in the fusion protein binds to the CIS element, thus forming a complex wherein the target component and the nucleic acid encoding the target component are linked via RepA.

In the nucleic acid encoding the target component (preferably DNA) to be used for the covalent antibody method (Nucleic Acids Res, 33(1), e10, 2005), endonuclease P2A gene is fused in-frame to the 3' end of the coding region of the target component via a spacer. By translation using the nucleic acid as a template, a fusion protein of the target component and P2A is produced, and P2A contained in the fusion protein is covalently bound to the DNA encoding the fusion protein, thus forming a complex wherein the target component and the nucleic acid encoding the target component are linked via P2A.

In the first embodiment, a protein multimer-nucleic acid complex comprising the protein multimer and the nucleic acid encoding the target component is obtained by adding a nucleic acid encoding a non-target component constituting the protein multimer together with the target component to the translation product obtained in step i) to perform translation of the nucleic acid encoding the non-target component into the non-target component to give the non-target component, and associating the non-target component with the target component contained in the target component-nucleic acid complex to form a protein multimer (step ii). For example, when an antibody-nucleic acid complex containing an antibody, and a nucleic acid encoding any one chain (target chain) (for example, L chain) selected from the component group consisting of H chain and L chain constituting the antibody is to be produced by the method of the present invention, a nucleic acid encoding a non-target chain (for example, H chain) constituting the antibody together with the target chain is added to translate the nucleic acid encoding the non-target chain into the non-target chain to give the non-target chain, and the non-target chain is associated with the target chain contained in the target chain-nucleic acid complex to form the antibody, whereby the antibody-nucleic acid complex containing the antibody, and the nucleic acid encoding the target chain is obtained.

The translation product obtained in step i) is expected to retain the in vitro translation activity even after completion of the translation in step i). Therefore, when a nucleic acid encoding a non-target component is added to the translation product obtained in step i), the nucleic acid is translated into the non-target component due to the remaining in vitro translation activity.

In the second embodiment, separately from step i'), a nucleic acid encoding a non-target component constituting the protein multimer together with the target component is translated into the non-target component by an in vitro translation system to give a translation product containing the non-target component (step ii'), and the translation product of i') is further mixed with the translation product of ii'), and the non-target component is associated with the target component contained in the target component-nucleic acid complex to form a protein multimer, whereby the protein multimer-nucleic acid complex comprising the protein multimer and the nucleic acid encoding the target component is obtained (step iii'). For example, when an antibody-nucleic acid complex containing an antibody, and a nucleic acid encoding any one chain (target chain) (for example, L chain) selected from the component group consisting of H chain and L chain constituting the antibody is to be produced by the method of the present invention, separately from the translation of the target chain, a nucleic acid encoding a non-target chain (for example, H chain) constituting the antibody together with the target chain is translated into the non-target chain by an in vitro translation system to give a translation product containing the non-target chain (for example, H chain), the translation product containing the target chain (for example, L chain)-nucleic acid complex and the translation product containing the non-target chain (for example, H chain) are mixed, and the non-target chain is associated with the target chain contained in the target chain-nucleic acid complex to form the antibody, whereby the antibody-nucleic acid complex containing the antibody, and the nucleic acid encoding the target chain is obtained.

The nucleic acid encoding the non-target component may be mRNA or cDNA. When the in vitro translation system used in step i) of the first embodiment does not contain an RNA polymerase to transcribe DNA to mRNA, the nucleic acid encoding the non-target component is preferably mRNA. This is because translation into a non-target component is possible even without newly adding an RNA polymerase. On the other hand, when the in vitro translation system used in step i) contains an RNA polymerase to transcribe DNA to mRNA, the nucleic acid encoding the non-target component may be any of mRNA and cDNA.

To improve the translation efficiency of a non-target component, when a ribosome derived from prokaryote such as *Escherichia coli* and the like is utilized in an in vitro translation system, a nucleic acid (preferably mRNA) encoding the non-target component preferably contains the SD sequence at the upstream of the initiation codon.

Since the nucleic acid encoding the non-target component does not need to be corresponded to the non-target component, modification of the nucleic acid therefor (addition of spacer to the downstream of the target gene, partial sequence of SecM to the downstream of spacer etc.) is not necessary.

Among the factors contained in the composition having an in vitro translation activity used in step i) of the first embodiment, the factor(s) consumed in the translation in step i) may be added to the translation product obtained in step i) together with the nucleic acid encoding the non-target component. As such factor, ribosome can be mentioned. Particularly, when a target component-ribosome-nucleic acid (preferably mRNA) ternary complex is formed in step i), the ribosome may be introduced into the ternary complex without being recycled and depleted from the in vitro translation system, and therefore, it is preferable to add, in step ii), ribosome to the translation product obtained in step i). Ribosome is added to the translation product obtained in step i) such that the concentration excluding ribosome contained in the above-mentioned ternary complex is, for example, 0.01 µM-50 µM preferably 0.05 µM-10 µM.

In step ii), the non-target component is produced by adding the nucleic acid encoding the non-target component to the translation product obtained in step i) and incubating the mixture at a temperature at which the in vitro translation proceeds, thus translating the nucleic acid into the non-target component. While the incubation time is not particularly limited as long as it is sufficient for completion of the translation of the nucleic acid into the non-target component, it is generally about 5-240 min. The produced non-target component is associated with the target component contained in the target component-nucleic acid complex in the reaction mixture to form a protein multimer, whereby a protein multimer-nucleic acid complex containing the protein multimer, and the nucleic acid encoding the target component can be obtained.

The embodiment of the composition having an in vitro translation activity, which is used in step ii') of the second embodiment is as described above as the embodiment of the composition having an in vitro translation activity, which is used in step i').

In step ii'), a translation product containing the non-target component can be produced by adding the nucleic acid encoding the non-target component to the above-mentioned composition having an in vitro translation activity and incubating the mixture at a temperature at which the in vitro translation proceeds, thus translating the nucleic acid into the non-target component. The incubation time is not particularly limited as long as it is sufficient for completion of the translation of the nucleic acid into the non-target component, it is generally about 5-240 min.

What is important here is that the in vitro translation in steps ii') is performed in the absence of the nucleic acid encoding the target component. Thus, a protein multimer-nucleic acid complex can be produced highly efficiently by performing the translation into the target component and that into the non-target component separately in different reaction systems, and thereafter mixing all translation products.

The protein multimer-nucleic acid complex comprising the protein multimer and the nucleic acid encoding the target component is obtained by further mixing the translation product of i') with the translation product of ii'), associating the non-target component with the target component contained in the target component-nucleic acid complex to form the protein multimer (step iii').

When a translation product containing a target component-ribosome-mRNA ternary complex is obtained by ribosome display in step i) or i'), a protein multimer-ribosome-mRNA ternary complex containing a protein multimer, mRNA encoding a target component and ribosome is obtained in step ii) or iii').

When a translation product containing a complex wherein the target component and the nucleic acid (preferably, mRNA) encoding the target component are covalently linked via puromycin is obtained by mRNA display in step i) or i'), a complex wherein the protein multimer and the nucleic acid (preferably, mRNA) encoding the target component are covalent linked via puromycin is obtained in step ii) or iii').

When a translation product containing a complex wherein the target component and the nucleic acid encoding the target component are linked via RepA is obtained by CIS display in step i) or i'), a complex wherein the protein multimer and the nucleic acid encoding the target component are linked via RepA is obtained in step ii) or iii').

When a translation product containing a complex wherein the target component and the nucleic acid encoding the target component are linked via P2A is obtained by a covalent antibody method in step i) or i'), a complex wherein the protein multimer and the nucleic acid encoding the target component are linked via P2A is obtained in step ii) or iii').

A protein multimer-nucleic acid complex produced by the method of the present invention contains one molecule of the protein multimer and one molecule of the nucleic acid encoding the target component, per molecule of the complex. That is, in the complex, since the protein multimer corresponds one-to-one to the nucleic acid encoding the component in the protein multimer, the nucleic acid encoding the component contained in the object protein multimer can be obtained by selecting a ternary complex containing a protein multimer having a desired activity such as specific binding to a particular target substance and the like and amplifying the nucleic acid contained in the ternary complex.

Although not restricted by theory, when a target component-nucleic acid-ribosome ternary complex containing the target component, the nucleic acid encoding the target component and ribosome is formed by translating the nucleic acid encoding the target component into the target component by ribosome display, ribosome turnover is suppressed, since ribosome is stably incorporated into the ternary complex. In contrast, the ribosome turnover actively occurs in the translation of the non-target component, since incorporation of ribosome into the complex does not occur. Therefore, when translation of the target component and that of the non-target component, showing opposite ribosome turnover conditions, are simultaneously performed in the same tube, regulation of ribosome may become inconsistent and the final product amount of the protein multimer-ribosome-nucleic acid ternary complex may decrease. In contrast, in the method of the present invention, the target component is first translated under an environment suppressing ribosome turnover to form a target component-nucleic acid-ribosome ternary complex, after which a non-target component is translated under a high ribosome turnover environment in the presence of a target component-nucleic acid-ribosome ternary complex (the first embodiment), or in a tube separated from the tube for the translation of the target component (the second embodiment). As a result, regulation of ribosome becomes consistent, and smooth and accurate association of the target component and the non-target component occurs. Consequently, there is a high possibility that a protein multimer-ribosome-nucleic acid ternary complex is formed with high efficiency.

In one aspect, a library of the nucleic acid encoding the target component can be used as the nucleic acid encoding the target component. In this case, in the first embodiment, the library of a protein multimer-nucleic acid complex comprising a protein multimer and a nucleic acid encoding a target component can be obtained by i) translating a library of a nucleic acid encoding the target component into the target component by an in vitro translation system to give a translation product containing a library of a target component-nucleic acid complex containing the target component and the nucleic acid encoding the target component, and ii) translating a nucleic acid encoding a non-target component constituting the protein multimer together with the target component into the non-target component by adding the nucleic acid encoding the non-target component to the translation product obtained in i) to give the non-target component, associating the non-target component with the target component in the target component-nucleic acid complex to form the protein multimer.

In the second embodiment, a library of a protein multimer-nucleic acid complex comprising a protein multimer and a nucleic acid encoding the target component can be obtained by i') translating a library of a nucleic acid encoding the target component into the target component by an in vitro translation system to give a translation product containing a library of a target component-nucleic acid complex containing the target component and the nucleic acid encoding the target component, ii') translating a nucleic acid encoding a non-target component constituting the protein multimer together with the target component by an in vitro translation system to give a translation product containing the non-target component, and iii') mixing the translation product of i') with the translation product of ii'), associating the non-target component with the target component contained in the target component-nucleic acid complex to form a protein multimer.

The present invention also provides a method of producing such library of a protein multimer-nucleic acid complex comprising a protein multimer and a nucleic acid encoding any one target component of the protein multimer.

In the present invention, the "library" refers to a population with diversity, which consists of a plurality of cloned nucleic acids. A nucleic acid that encodes a target component contained in a protein multimer having a desired property can be obtained from a library using an in vitro selection system such as ribosome display. The library of nucleic acids usable in the present invention includes a cDNA library, an mRNA library, and a genomic DNA library. In prokaryotic cells and yeast cells, usually no intron is present in most genes. Therefore, in the case of prokaryotic cells and yeast cells, a genomic DNA library can be utilized to directly screen for a nucleic acid that encodes a protein having the desired property from proteins derived from the cells. In higher eukaryotes such as mammals, conversely, an intron is present in most genes, so that an mRNA library or a cDNA library is usually utilized.

The sequences of nucleic acids that constitute the library can comprise not only sequences of natural origin, but also artificially introduced sequences. For example, libraries incorporating mutations are included in the library in the present invention. Alternatively, a library comprising sequences prepared by joining an artificial sequence to a sequence of natural origin is also included in the library in the present invention. Furthermore, a library comprising a completely artificially designed sequence is also included in the library in the present invention.

Moreover, by contacting the complex obtained by step ii') or step iii') with a target substance, and evaluating the affinity of the protein multimer contained in the complex for the target substance, a protein multimer having affinity for the desired target substance can be selected and the nucleic acid sequence of the target component contained in the protein multimer can be identified. In the present invention, the "target substance" refers to a substance to which the desired protein multimer can bind. In the present invention, any substance to which a protein multimer may bind can be utilized as the target substance. The target substances of the present invention include, for example, nucleic acids, polypeptides, organic compounds, inorganic compounds, low-molecular weight compounds, sugar chains, fats, and lipids. More specifically, a substance that functions as an antigen or hapten can be utilized as the target substance. In this case, the desired antibody can be screened from an antibody library, and the sequence of the nucleic acid encoding one of the L chain and the H chain contained in the antibody can be determined.

Conditions for contacting a protein multimer-nucleic acid complex with a target substance to enable their binding are publicly known (WO95/11922, WO93/03172, WO91/05058), and can be established without excess burdens by those skilled in the art. In order to recover the complex bound to the target substance, it is necessary to screen for the complex bound to the target substance from among complexes not bound to the target substance. This is performed according to a known method called panning (Coomber, Method Mol. Biol. (2002) vol. 178, p. 133-145). The basic procedures for panning are as described below.

(1) The complex is contacted with the target substance immobilized on a solid phase carrier. Alternatively, the complex is contacted with the target substance labeled with a binding partner to be captured by a solid phase carrier, after which the target substance bound to the complex is immobilized onto the solid phase carrier.

(2) The complexes not bound to the target substance are removed. For example, the same can be removed by washing.

(3) The complex that has not been removed is recovered.

(4) The processes (1) to (3) are repeated a plurality of times as required.

When repeating the series of steps, it is also possible to amplify the mRNA that constitutes the recovered complex before the step (1). The mRNA can be amplified by, for example, RT-PCR. DNA is synthesized by RT-PCR with the mRNA as the template. The DNA may be transcribed again to an mRNA, and can be utilized for forming the complex. For mRNA transcription, DNA can be inserted into a vector. Alternatively, the structure necessary for the transcription may be joined to DNA to transcribe to mRNA.

In the present specification, "screening" refers to selecting an entity with the desired property from among substances synthesized by a chemical synthesis, an enzymatic reaction or a combination thereof, substances prepared from extracts of various cells, or naturally occurring substances. "Cloning" refers to isolating a particular gene.

After the complex that presents the desired protein multimer is selected, the sequence of the nucleic acid that encodes the target component contained in the complex can be identified. At the stage when the complex is selected, the nucleic acid that encodes the target component is an mRNA. By synthesizing a cDNA using a reverse transcriptase with this mRNA as the template, and reading the nucleic acid sequence using a sequencer, the nucleic acid sequence thereof can be determined. These techniques are publicly known.

The contents disclosed in any publication cited herein, including patents and patent applications, are hereby incorporated in their entireties by reference, to the extent that they have been disclosed herein.

The present invention is explained in more detail in the following by referring to Examples, which are not to be construed as limitative.

EXAMPLES

Example 1

<Method>

Construction of Anti-TNF-α Antibody Gene for Ribosome Display

The genes of the H and L chains of an anti-TNF-α antibody were chemically synthesized (GenScript) by reference to JP-B-3861118, and at that time, FLAG tag sequence+stop codon was added to the 3' terminus of the H chain, and c-Myc tag sequence was added to the 3' terminus of the L chain.

H chain:
(SEQ ID NO: 1)
ATGGAGGTGCAATTGGTGGAGTCTGGGGGAGGCTTGGTACAGCCCGGCAGGTCCCTGAGACT

CTCCTGTGCGGCCTCTGGATTCACCTTTGATGATTATGCCATGCACTGGGTCCGGCAAGCTC

CAGGGAAGGGCCTGGAATGGGTCTCAGCTATCACTTGGAATAGTGGTCACATAGACTATGCG

GACTCTGTGGAGGGCCGATTCACCATCTCCAGAGACAACGCCAAGAACTCCCTGTATCTGCA

AATGAACAGTCTGAGAGCTGAGGATACGGCCGTATATTACTGTGCGAAAGTCTCGTACCTTA

GCACCGCGTCCTCCCTTGACTATTGGGGCCAAGGGACCCTGGTCACCGTCTCGAGTGCTAGC

TTCAAGGGCCCATCGGTCTTCCCCCTGGCACCCTCCTCCAAGAGCACCTCTGGGGGCACAGC

GGCCCTGGGCTGCCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGT

GAATCACAAGCCCAGCAACACCAAGGTGGACAAGAGAGTTGAGCCCAAATCTGAATTCGACT

ATAAAGATGACGATGACAAATAATGA

L chain:
(SEQ ID NO: 2)
ATGGATATCCAGATGACCCAGTCTCCATCCTCCCTGTCTGCATCTGTAGGGGACAGAGTCAC

CATCACTTGTCGGGCAAGTCAGGGCATCAGAAATTACTTAGCCTGGTATCAGCAAAAACCAG

GGAAAGCCCCTAAGCTCCTGATCTATGCTGCATCCACTTTGCAATCAGGGGTCCCATCTCGG

TTCAGTGGCAGTGGATCTGGGACAGATTTCACTCTCACCATCAGCAGCCTACAGCCTGAAGA

TGTTGCAACTTATTACTGTCAAAGGTATAACCGTGCACCGTATACTTTTGGCCAGGGGACCA

AGGTGGAAATCAAACGAACTGTGGCGGCGCCATCTGTCTTCATCTTCCCGCCATCTGATGAG

CAGTTGAAATCTGGAACTGCCTCTGTTGTGTGCCTGCTGAATAACTTCTATCCTCGAGAGGC

CAAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGAT

TACGAGAAACACAAAGTCTACGCCTGCGAAGTCACCCATCAGGGCCTGAGCTCGCCCGTCAC

AAAGAGCTTCAACAGGGGAGAGGAGCAGAAGCTGATCTCTGAGGAGGATCTGCAT

In addition, 5' UTR sequence containing T7 promoter and the SD sequence necessary for the expression with in vitro translation system from *Escherichia coli* were also synthesized chemically (Sigma).

H chain 5' UTR:
(SEQ ID NO: 3)
gaaattaatacgactcactatagggagaccacaacggtttccctctagaaataattttgttt aactttaagaaggagatataccaATGGAGGTGCAATTGGTGGAGTCTGGGGGAG L chain 5' UTR:
(SEQ ID NO: 4)
gaaattaatacgactcactatagggagaccacaacggtttccctctagaaataattttgttt aactttaagaaggagatataccaATGGATATCCAGATGACCCAGTCTCCATCCTCCCTG A partial sequence (the 220-326th amino acid residues) of geneIII (g3p) of M13 phage was amplified by PCR using M13KO7-phage genome as a template and the following primer set, with KOD Plus DNA Polymerase (TOYOBO)

(denaturation: 94° C., 10 sec, annealing: 58° C., 30 sec, extension: 68° C., 60 sec, cycles: 25), and the product was purified using a QIAquick PCR purification kit (QIAGEN).

primer myc-g3p:
(SEQ ID NO: 5)
GAGCAGAAGCTGATCTCTGAGGAGGATCTGCATGAATATCAAGGCCAATCGTCTGAC primer g3p-SecMstop:
(SEQ ID NO: 6)
CTCGAGTTATTCATTAGGTGAGGCGTTGAGGGCCAGCACGGATGCCTTGCGCCTGGCTTATC

CAGACGGGCGTGCTGAATTTTGCGCCGGAAACGTCACCAATGAAAC

A PCR reaction mixture (total 500 µL) containing respective chemically-synthesized gene fragments (H chain 5'UTR and H chain, each 1 pmol), 5' primer: GAAATTAATAC-GACTCACTATAGGGAGACCACAACG-GTTTCCCTCTAG (SEQ ID NO: 7, 10 pmol), FLAG stop R: TCATTATTTGTCATCGTCATCTTTATAGTCG (SEQ ID NO: 8, 10 pmol), and KOD Plus DNA Polymerase (TOYOBO) was prepared, and 25 cycles of PCR reaction (denaturation: 94° C., 10 sec, annealing: 58° C., 30 sec, extension: 68° C., 60 sec) were performed. A band in which two genes were connected was confirmed by electrophoresis using 1% agarose, and the band was excised and purified by a MinElute Gel Extraction Kit (QIAGEN) to finally give an H chain gene. In addition, in the same manner, a PCR reaction solution (total 500 µL) containing respective chemically-synthesized gene fragments (L chain 5'UTR and L chain) and g3p gene (each 1 pmol), 5' primer: GAAATTAATACGACTCAC-TATAGGGAGACCACAACGGTTTCCCTCTAG (SEQ ID NO: 7, 10 pmol), primer SecMstop: GGATTAGTTAT-TCATTAGGTGAGGCGTTGAGG (SEQ ID NO: 9, 10 pmol), and KOD Plus DNA Polymerase (TOYOBO) was prepared, and 25 cycles of PCR reaction (denaturation: 94° C., 10 sec, annealing: 58° C., 30 sec, extension: 68° C., 60 sec) were performed. A band in which all genes were connected was confirmed by electrophoresis using 1% agarose, and the band was excised and purified by a MinElute Gel Extraction Kit (QIAGEN) to finally give an L chain gene.

In Vitro Transcription

The purified H, L chain gene DNA (1 µg) was transcribed into mRNA by 20 µL of in vitro transcription Kit (Ribomax™ Large Scale RNA Production System-T7, Promega), and purified by a column (RNeasy mini column, QIAGEN).

Formation of Ribosome Display Complex

The in vitro translation system (PURE system), which is a protein synthesis reaction reagent, was prepared according to a previous report (Shimizu et al. (2005) Methods, vol. 36, p 299-304).

(Condition 1)

To the prepared reaction mixture (10 µL) were added oxidized glutathione (GSSG: Sigma Ltd.) at a final concentration of 3 mM, Escherichia coli DsbC protein at a final concentration of 1 µM prepared in advance, L chain-g3p mRNA (1 pmol), and H chain mRNA (1 pmol), and the mixture was incubated at 30° C. for 60 min.

(Condition 2)

To the prepared reaction mixture (5 µL) were added oxidized glutathione (GSSG: Sigma Ltd.) at a final concentration of 3 mM, Escherichia coli DsbC protein at a final concentration of 1 µM prepared in advance, and L chain-g3p mRNA (1 pmol), and the mixture was incubated at 30° C. Simultaneously, to the prepared reaction mixture (5 µL) were added oxidized glutathione (GSSG: Sigma Ltd.) at a final concentration of 3 mM, Escherichia coli DsbC protein at a final concentration of 1 µM prepared in advance, and H chain mRNA (1 pmol), and the mixture was incubated at 30° C. Each was incubated for 30 min, respective reaction mixtures were mixed, and the mixture was further incubated at 30° C. for 30 min.

(Condition 3)

To the prepared reaction mixture (10 µL) were added oxidized glutathione (GSSG: Sigma Ltd.) at a final concentration of 3 mM, Escherichia coli DsbC protein at a final concentration of 1 µM prepared in advance, and L chain-g3p mRNA (1 pmol), and the mixture was incubated at 30° C. After 30 min, H chain mRNA (1 pmol) and ribosome (5 pmol) were added, and the mixture was further incubated at 30° C. for 30 min.

In respective conditions, 500 µL of ice-cooled Wash buffer (50 mM Tris-OAc, pH 7.5, 150 mM NaCl, 25 mM Mg(OAc)$_2$, 0.5% Tween 20, 1 µg/mL Saccharomyces cerevisiae total RNA (Sigma) was added to the translation solution to terminate the translation.

Biotinylation of Antigen Protein

Purchased TNF-α protein (TOYOBO) was biotinylated according to the standard protocol for EZ-Link NHS-PEO$_4$-Biotin (PIERCE). Biotinylation of each biotinylated antigen protein was confirmed by the mobility shift of the band in SDS-PAGE, and the concentration was determined using a BCA Protein Assay Kit (PIERCE).

In Vitro Selection

Dynabeads MyOne streptavidin T1 magnetic beads (10 µL slurry, Invitrogen) blocked in advance with 5% SuperBlock (Thermo scientific) at 4° C. overnight were washed twice with 500 µL of Wash buffer using MagneSphere Magnetic Separation Stand (Promega), 1 nmol biotinylated TNF-α protein was added, and immobilized on the magnetic beads at 4° C. After 30 min, the magnetic beads were washed three times with 500 µL of Wash buffer using MagneSphere Magnetic Separation Stand (Promega), the translation solution was added to the recovered magnetic beads, and the mixture was stirred at 4° C. for 1 hr by rotation. The supernatant was discarded using MagneSphere Magnetic Separation Stand (Promega), 1 mL of Wash buffer was added to the recovered magnetic beads, and the mixture was stirred at 4° C. for 5 min by rotation. This operation was repeated 30 times, 50 µL of Elution buffer (50 mM Tris-OAc, pH 7.5, 150 mM NaCl, 50 mM EDTA) was added to the recovered magnetic beads, and the mixture was left standing at 4° C. for 10 min to allow release of the complex from the magnetic beads. The supernatant was collected with MagneSphere Magnetic Separation Stand (Promega), and mRNA was collected and purified by RNeasy Micro (QIAGEN).

Real Time PCR

After in vitro selection, a reaction mixture containing the recovered mRNA (1 µL), primer Realtime-F: GAGCAAAG-CAGATTACGAGAAACAC (SEQ ID NO: 10), primer Myc-R: CAGATCCTCCTCAGAGATCAGC (SEQ ID NO: 11) and RNA-direct SYBR Green Realtime PCR Master Mix (TOYOBO) was prepared, and the final mRNA amount was quantified according to the standard protocol using LightCycler (Roche).

<Results>

Figure 1:
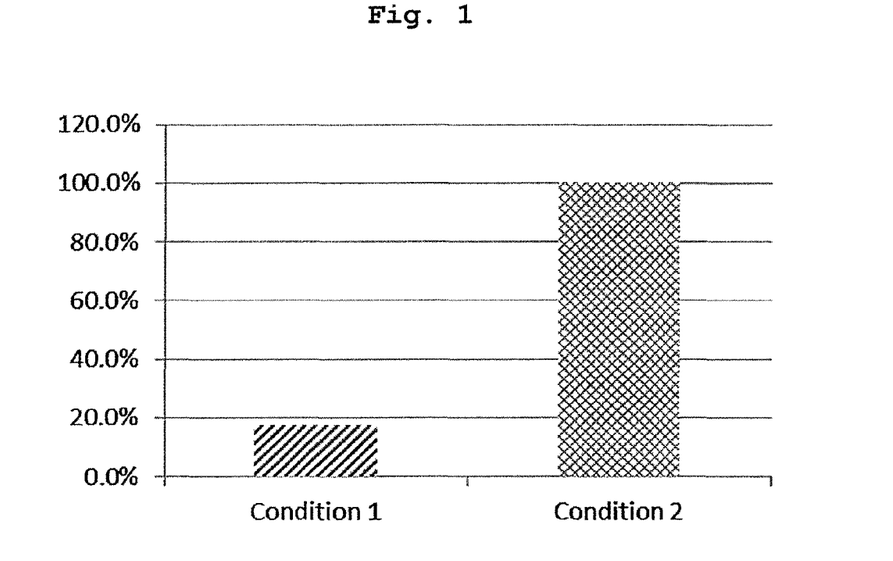
FIG. 1 shows comparison of the amount of mRNA recovery from the ribosome display complexes formed under two different conditions (conditions 1 and 2) in percent.
Figure 2:
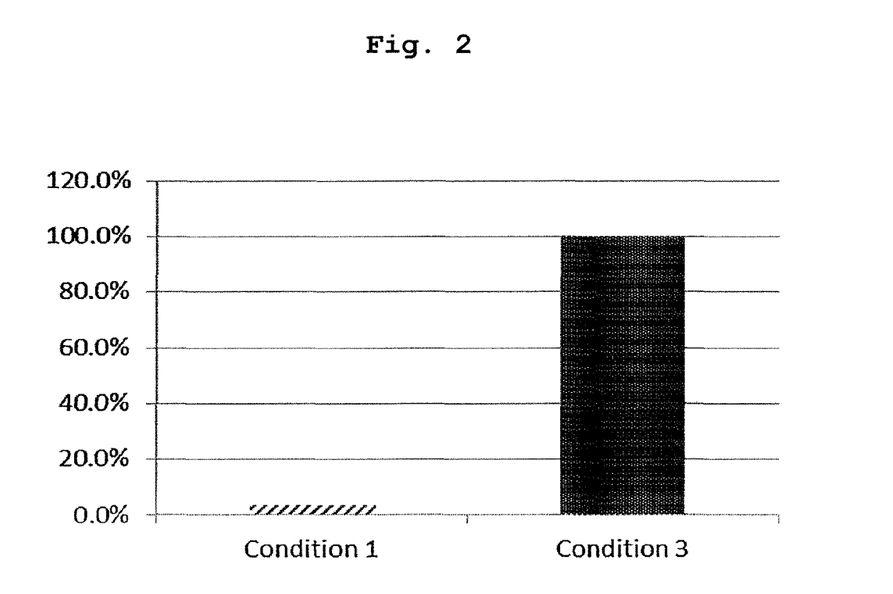
FIG. 2 shows comparison of the amount of mRNA recovery from the ribosome display complexes formed under two different conditions (conditions 1 and 3) in percent.

FIG. 1 shows comparison of the amounts of mRNA recovered by in vitro selection after translation under respective conditions 1 and 2, wherein the amount under condition 2 was indicated as 100%. As a result, there was about 5-fold difference in the mRNA recovery amount between condition 1 and condition 2. FIG. 2 shows comparison of the amounts of mRNA obtained under respective conditions 1 and 3 in the same manner as in FIG. 1, wherein the amount under condition 3 was indicated as 100%. As a result, there was about 28-fold difference between condition 1 and condition 3.

These results have clarified that a ribosome display complex containing a protein multimer can be formed at high efficiency, and the mRNA recovery rate after selection is drastically improved by first forming a ribosome display complex for a library gene (L chain of antibody here) in an in vitro translation system and expressing a pair protein gene (H chain of antibody here) in the same tube, or forming a ribosome display complex for a library gene (L chain of antibody here) and translating a pair protein gene (H chain of antibody here) in separated tubes in an in vitro translation system, and mixing all the translation products.

INDUSTRIAL APPLICABILITY

According to the present invention, a method of efficiently displaying a protein multimer on a display complex so as to select a nucleic acid encoding a component contained in the protein multimer having a desired function from the library is provided. By performing in vitro selection such as ribosome display, mRNA display and the like using the present invention, the function such as binding affinity and the like of a complicated protein multimer such as antibody and the like can be increased or improved efficiently.

This application is based on U.S. provisional patent application No. 61/638,774 (filing date: Apr. 26, 2012), the contents of which are encompassed in full herein.

The invention claimed is:

1. A method of producing a protein multimer-nucleic acid complex comprising the protein multimer and a nucleic acid encoding any one target component of the protein multimer, which comprises the following steps: i) translating a nucleic acid encoding the target component into the target component by an in vitro translation system to give a translation product containing a target component-nucleic acid complex containing the target component and the nucleic acid encoding the target component, and ii) translating a nucleic acid encoding a non-target component constituting the protein multimer together with the target component into the non-target component by adding the nucleic acid encoding the non-target component to the translation product obtained in i) to give the non-target component, associating the non-target component with the target component in the target component-nucleic acid complex to form the protein multimer, thus affording the protein multimer-nucleic acid complex comprising the protein multimer and the nucleic acid encoding the target component, wherein the target component is a component of interest among components constituting the protein multimer, and the non-target component is a component other than the target component, constituting the protein multimer together with the target component.

2. The method according to claim 1, wherein the in vitro translation system in i) does not comprise a nucleic acid encoding the non-target component.

3. The method according to claim 1, wherein the protein multimer-nucleic acid complex and the target component-nucleic acid complex comprise a ribosome.

4. The method according to claim 1, wherein ii) comprises adding a ribosome to the translation product obtained in i).

5. The method according to claim 1, wherein one molecule of the protein multimer and one molecule of the nucleic acid encoding the target component are contained per one molecule of the protein multimer-nucleic acid complex.

6. The method according to claim 1, wherein the in vitro translation system consists of independently purified factors.

7. The method according to claim 6, wherein at least one of the independently purified factors is a factor extracted from prokaryote.

8. The method according to claim 1, wherein the protein multimer is a dimer.

9. The method according to claim 1, wherein the protein multimer has a function as a multimer.

10. The method according to claim 1, wherein the protein multimer is an antibody.

11. The method according to claim 10, wherein the antibody is a Fab fragment.

12. The method according to claim 10, wherein the target component is one selected from the group consisting of an L chain and an H chain, and the non-target component is the other.

13. The method according to claim 1, wherein the nucleic acid encoding the target component is a library of the nucleic acid encoding the target component.

14. A method of producing a library of a protein multimer-nucleic acid complex comprising the protein multimer and a nucleic acid encoding any one target component of the protein multimer, which comprises the following steps: i) translating a library of nucleic acid encoding the target component into the target component by an in vitro translation system to give a translation product containing a library of a target component-nucleic acid complex containing the target component and the nucleic acid encoding the target component, and ii) translating a nucleic acid encoding a non-target component constituting the protein multimer together with the target component into the non-target component by adding the nucleic acid encoding the non-target component to the translation product obtained in i) to give the non-target component, associating the non-target component with the target component in the target component-nucleic acid complex to form the protein multimer, thus affording the library of the protein multimer-nucleic acid complex comprising the protein multimer and the nucleic acid encoding the target component, wherein the target component is a component of interest among components constituting the protein multimer, and the non-target component is a component other than the target component, constituting the protein multimer together with the target component.

15. The method according to claim 14, wherein the in vitro translation system in i) does not comprise a nucleic acid encoding the non-target component.

16. The method according to claim 14, wherein the protein multimer-nucleic acid complex and the target component-nucleic acid complex comprise a ribosome.

17. The method according to claim 14, wherein ii) comprises adding a ribosome to the translation product obtained in i).

18. The method according to claim 14, wherein one molecule of the protein multimer and one molecule of the nucleic acid encoding the target component are contained per one molecule of the protein multimer-nucleic acid complex.

19. The method according to claim 14, wherein the in vitro translation system consists of independently purified factors.

20. The method according to claim 19, wherein at least one of the independently purified factors is a factor extracted from prokaryote.

21. The method according to claim 14, wherein the protein multimer is a dimer.

22. The method according to claim 14, wherein the protein multimer has a function as a multimer.

23. The method according to claim 14, wherein the protein multimer is an antibody.

24. The method according to claim 23, wherein the antibody is a Fab fragment.

25. The method according to claim 23, wherein the target component is one selected from the group consisting of an L chain and an H chain, and the non-target component is the other.

26. The method according to claim 14, wherein the nucleic acid encoding the target component is a library of the nucleic acid encoding the target component.

* * * * *